(12) United States Patent
Mizuguchi

(10) Patent No.: US 8,268,250 B2
(45) Date of Patent: Sep. 18, 2012

(54) PROTON ACCEPTANCE TYPE SENSOR, HYDROGEN GAS SENSOR AND ACID SENSOR

(75) Inventor: Jin Mizuguchi, Kanagawa (JP)

(73) Assignee: Murata Manufacturing Co., Ltd., Kyoto (JP)

( * ) Notice: Subject to any disclaimer, the term of this patent is extended or adjusted under 35 U.S.C. 154(b) by 125 days.

(21) Appl. No.: 12/563,316

(22) Filed: Sep. 21, 2009

(65) Prior Publication Data

US 2010/0187109 A1    Jul. 29, 2010

Related U.S. Application Data

(63) Continuation of application No. 10/576,725, filed as application No. PCT/JP2004/014102 on Sep. 27, 2004, now abandoned.

(30) Foreign Application Priority Data

Oct. 22, 2003  (JP) .................................. 2003-362412
May 13, 2004  (JP) .................................. 2004-144138

(51) Int. Cl.
  *G01N 7/00*  (2006.01)
(52) U.S. Cl. ............ 422/83; 422/88; 324/693; 73/31.05
(58) Field of Classification Search .................... 422/83, 422/88; 324/693; 73/31.05
  See application file for complete search history.

(56) References Cited

U.S. PATENT DOCUMENTS

| | | |
|---|---|---|
| 4,313,338 A | 2/1982 | Abe et al. |
| 4,608,549 A | 8/1986 | Fukui |
| 4,717,673 A | 1/1988 | Wrighton et al. |
| 4,721,601 A | 1/1988 | Wrighton et al. |
| 4,895,705 A | 1/1990 | Wrighton et al. |
| 4,929,313 A | 5/1990 | Wrighton |
| 5,034,192 A | 7/1991 | Wrighton et al. |
| 5,273,841 A | 12/1993 | Yamamoto et al. |
| 5,316,852 A | 5/1994 | Mizuguchi et al. |
| 5,331,287 A | 7/1994 | Yamagishi et al. |
| 5,561,232 A * | 10/1996 | Hao et al. ........................ 546/14 |
| 5,779,783 A * | 7/1998 | Senba et al. .................. 106/410 |
| 2003/0019400 A1* | 1/2003 | Deckers et al. ............... 106/502 |

(Continued)

FOREIGN PATENT DOCUMENTS

EP    0 185 941 A2    7/1986

(Continued)

OTHER PUBLICATIONS

Office Action issued in connection with patent family member EP 04 788 198.2, dated Nov. 26, 2009.

(Continued)

*Primary Examiner* — Jill Warden
*Assistant Examiner* — Monique Cole
(74) *Attorney, Agent, or Firm* — Greenblum & Bernstein, P.L.C.

(57) ABSTRACT

The present invention provides a low-cost hydrogen gas sensor, which exhibits high sensory selectivity for protons and operates at room temperature, and can also provide a highly sensitive sensor capable of fulfilling the important functions of detecting hydrogen gas and preventing leakage accidents in production plants that use hydrogen gas as a carrier, in hydrogen gas storage facilities, and in so-called fuel cells that use hydrogen gas as an energy source. In addition, the sensor is also effective as an acid sensor for hydrofluoric acid and the like.

21 Claims, 7 Drawing Sheets

U.S. PATENT DOCUMENTS

2003/0153088 A1     8/2003    DiMeo, Jr. et al.

FOREIGN PATENT DOCUMENTS

| | | |
|---|---|---|
| EP | 0 530 145 | 3/1993 |
| FR | 2 783 051 | 3/2000 |
| JP | 57-120847 | 7/1982 |
| JP | 59-120945 | 7/1984 |
| JP | 62-011159 | 1/1987 |
| JP | 1-250851 | 10/1989 |
| JP | 3-075551 | 3/1991 |
| JP | 5-010908 | 1/1993 |
| JP | 6-160319 | 6/1994 |
| JP | 9-249815 | 9/1997 |
| JP | 2003-240746 | 8/2003 |

OTHER PUBLICATIONS

English Language Abstract of JP 2003-240746.
English Language Abstract of JP 57-120847.
English Language Abstract of JP 3-075551.
English Language Abstract of JP 9-249815.
English Language Abstract of JP 5-010908.
English Language Abstract of JP 6-160319.
English Language Abstract of JP 59-120945.
English Language Abstract of JP 1-250851.
Hiroo Takahashi et al., "Dipyridyl pyrrolo prytole no Kessho Takei to Denshi Kozo," Japan Hardcopy 2002 Fall Meeting Dai 90 Kai Nihon Gazo Gakkai Kenkyu Toronkai, pp. 53-56, 2002.
Jin Mizuguchi, "Solution and Solid State Properties of 1, 4-Diketo-3, 6-bis-(4'-pyridyl)-pyrrolo-[3,4-c]-pyrrole on Protonation and Deprotonation," Ber. Bunsenges. Phys. Chem., 1993, No. 97, vol. 5, pp. 684-693.
I. Eisele et al., "Low Power Gas Detection with FET Sensors," Sensors and Actuators B., vol. 78, 2001, pp. 19-25.
Supplementary European Search Report for EP 04 78 8198, Sep. 3, 2009.

\* cited by examiner

PROTON ACCEPTANCE TYPE SENSOR, HYDROGEN GAS SENSOR AND ACID SENSOR

CROSS-REFERENCE TO RELATED APPLICATION

This application is a continuation of application Ser. No. 10/576,725, which is the U.S. National Stage of PCT/JP2004/014102, filed Sep. 27, 2004, which are hereby incorporated by reference in their entirety.

TECHNICAL FIELD

The present invention relates to a sensor with favorable sensory selectivity for protons ($H^+$), and relates particularly to a hydrogen gas sensor and an acid sensor.

BACKGROUND ART

In recent years, the use of a variety of gases within the production processes for products has become common, and in production plants for semiconductors, because gas-based chemical reaction processes are employed on single crystal silicon substrates, volatile or toxic gases are widely used. Hydrogen gas is used in large quantities as the carrier gas for these gases. However, hydrogen gas is itself highly explosive, and any leaks of hydrogen gas must be detected immediately.

In addition, there is now much concern about the depletion of fossil fuels such as petroleum, and many different options are being researched as potential replacement energy sources. Hydrogen can be readily obtained by the electrolysis of water, and generates water as a combustion product, with no emission of $CO_2$, $NO_x$ or $SO_x$ or the like, and can consequently be claimed to be a very superior next-generation energy source.

In terms of techniques for converting hydrogen energy into electrical power, fuel cells that use the chemical reaction between hydrogen and oxygen are attracting the most attention. In particular, fuel cell vehicles fitted with fuel cells are being viewed with considerable hope as likely "favorites for environmentally friendly vehicles". However, because hydrogen is the lightest and smallest molecule it is prone to leakage, and because it also ignites readily and combusts rapidly, it is an extremely dangerous gas. As a result, if a hydrogen energy system develops in the future, then the positioning of hydrogen gas sensors can be expected to become increasingly important.

Currently, semiconductor-based sensors that use a metal oxide are the most representative hydrogen gas sensors. Although these sensors exhibit high sensitivity and a high level of reliability, the sensor element itself must be heated to a high temperature. As a result, there are limits on the levels of miniaturization, weight reduction, power consumption reduction, or cost reductions that can be achieved for this type of sensor, and it is thought that these sensors will be unsuitable for a large variety of applications.

A specific example of a hydrogen gas sensor is that disclosed in Japanese Patent Laid-Open No. Sho 59-120945. This publication proposes a hydrogen gas sensor comprising a pair of opposing electrodes formed on one surface of an insulating substrate, a gas-sensitive film ($SnO_2$) that covers these electrodes, a heater fitted to the opposite surface of the substrate, lead wires connected to this heater, and a catalyst layer (such as Pt) formed on top of the gas-sensitive film. However, in this hydrogen gas sensor, because the catalyst layer is formed by screen printing, controlling the film thickness is difficult, leading to large fluctuations in the film thickness, and making control of the properties of the sensor difficult. In addition, this hydrogen gas sensor also suffers from the drawback of having a high operating temperature of approximately 400° C.

Furthermore, in a semiconductor production plant, for example, isopropyl alcohol is used as a cleaning agent, and is always present in gaseous form in the air. Under these types of conditions, reliably detecting hydrogen gas leakage can be difficult, and as a result, providing a non-gas-sensitive thin film layer (an oxide such as $SiO_2$ or alumina or the like) on top of the gas-sensitive film has been proposed, as in Japanese Patent Laid-Open No. Hei 01-250851, but the process for producing this non-gas-sensitive thin film layer is difficult, meaning cost increases are unavoidable, and the control costs associated with controlling the properties of the sensor also increase.

In addition, there have been reports of gas detection elements that use a vapor deposition film of phthalocyanine, but these elements are used for monitoring the level of electrical conductivity accompanying gas adsorption and desorption, exhibit no selectivity between electron-donating and electron-withdrawing gases, and suffer from extremely unstable operation.

DISCLOSURE OF INVENTION

The present invention has been developed in view of the conventional technology described above, and provides a low-cost proton acceptance type gas sensor such as a hydrogen sensor or acid sensor, which exhibits favorable sensory selectivity for protons, and operates at room temperature.

The present invention relates to a proton acceptance type gas sensor, wherein protons are brought into contact with an organic compound containing an introduced heterocycle comprising a nitrogen atom, and the change in electrical resistivity, photoconductivity, or optical absorption band for the organic compound that accompanies proton addition is detected.

Furthermore, the present invention also relates to the above proton acceptance type gas sensor, wherein the heterocycle comprising a nitrogen atom is a pyridine-based heterocycle.

Furthermore, the present invention also relates to the above proton acceptance type gas sensor, wherein the organic compound is an organic pigment containing an introduced heterocycle comprising a nitrogen atom.

Furthermore, the present invention also relates to a hydrogen gas sensor, wherein protons are brought into contact with an organic compound containing an introduced pyridine ring, and the change in electrical resistivity, photoconductivity, or optical absorption band for the organic compound that accompanies proton addition is detected.

Furthermore, the present invention also relates to the above hydrogen gas sensor, wherein the organic compound is an organic pigment containing an introduced pyridine ring.

Furthermore, the present invention also relates to the above hydrogen gas sensor, wherein the organic pigment is a pyrrolo-pyrrole, quinacridone, indigo, phthalocyanine, anthraquinone, indanthrone, anthanthrone, perylene, pyrazolone, perinone, isoindolinone, isoindoline, dioxazine, or a derivative thereof.

Furthermore, the present invention also relates to the above hydrogen gas sensor, wherein the organic compound and a protonation catalyst for hydrogen gas are brought into contact.

Furthermore, the present invention also relates to the above hydrogen gas sensor, wherein the protonation catalyst is Pt, Pd, Ni, a two-component alloy thereof, or a three-component alloy thereof.

Furthermore, the present invention also relates to the above hydrogen gas sensor, wherein a film of an organic pigment that acts as a sensitivity promoter is layered to either one surface or both surfaces of the film of the organic compound.

Furthermore, the present invention also relates to the above hydrogen gas sensor, wherein at least one pair of electrodes is positioned in contact with the film of the organic compound, and the change in electrical resistivity or photoconductivity is detected.

Furthermore, the present invention also relates to the above hydrogen gas sensor, wherein the film of the organic compound is a vacuum deposition film or a sputtered film.

Furthermore, the present invention also relates to the above hydrogen gas sensor, which is an element in which at least one pair of electrodes is positioned in an opposing arrangement on top of a substrate, the above film of the organic compound is disposed thereon, and either a protonation catalyst contacts one surface or both surfaces of the film of the organic compound, or a protonation catalyst is distributed through the film of the organic compound, wherein the sensor is an electrical resistance-mode sensor that detects changes in the electrical resistivity between the electrodes.

Furthermore, the present invention also relates to the above hydrogen gas sensor, wherein the protonation catalyst is provided in an islands-type arrangement, using a vacuum deposition method or a sputtering method, either on top of the substrate and the electrodes, or on top of the film of the organic compound, or within the film of the organic compound.

Furthermore, the present invention also relates to the above hydrogen gas sensor, having a field-effect transistor (FET) structure in which a $n^+$-Si substrate functions as the gate, the source and drain electrodes are formed on top of the substrate with a silicon oxide insulating film disposed therebetween, and the film of the organic compound is formed on top of the silicon oxide and the electrodes.

Furthermore, the present invention also relates to the above hydrogen gas sensor, wherein the sensor is a photoconduction-mode sensor that includes an excitation light source and detects changes in photoconductivity.

Furthermore, the present invention also relates to the above hydrogen gas sensor, wherein the sensor is an optical absorption band-mode sensor that includes a photodiode or a photomultiplier and detects changes in the optical absorption band.

Furthermore, the present invention also relates to an acid sensor, wherein protons are brought into contact with an organic compound containing an introduced pyridine ring, and the change in electrical resistivity, photoconductivity, or optical absorption band for the organic compound that accompanies proton addition is detected.

Furthermore, the present invention also relates to the above acid sensor, wherein the organic compound is an organic pigment containing an introduced pyridine ring.

Furthermore, the present invention also relates to the above acid sensor, wherein the organic pigment is a pyrrolo-pyrrole, quinacridone, indigo, phthalocyanine, anthraquinone, indanthrone, anthanthrone, perylene, pyrazolone, perinone, isoindolinone, isoindoline, dioxazine, or a derivative thereof.

This Application is based upon and claims the benefit of priority from prior Japanese Application 2003-362412 filed on Oct. 22, 2003 and prior Japanese Application 2004-144138 filed on May 13, 2004; the entire contents of which are incorporated by reference herein.

BEST MODE FOR CARRYING OUT THE INVENTION

Figure 1:
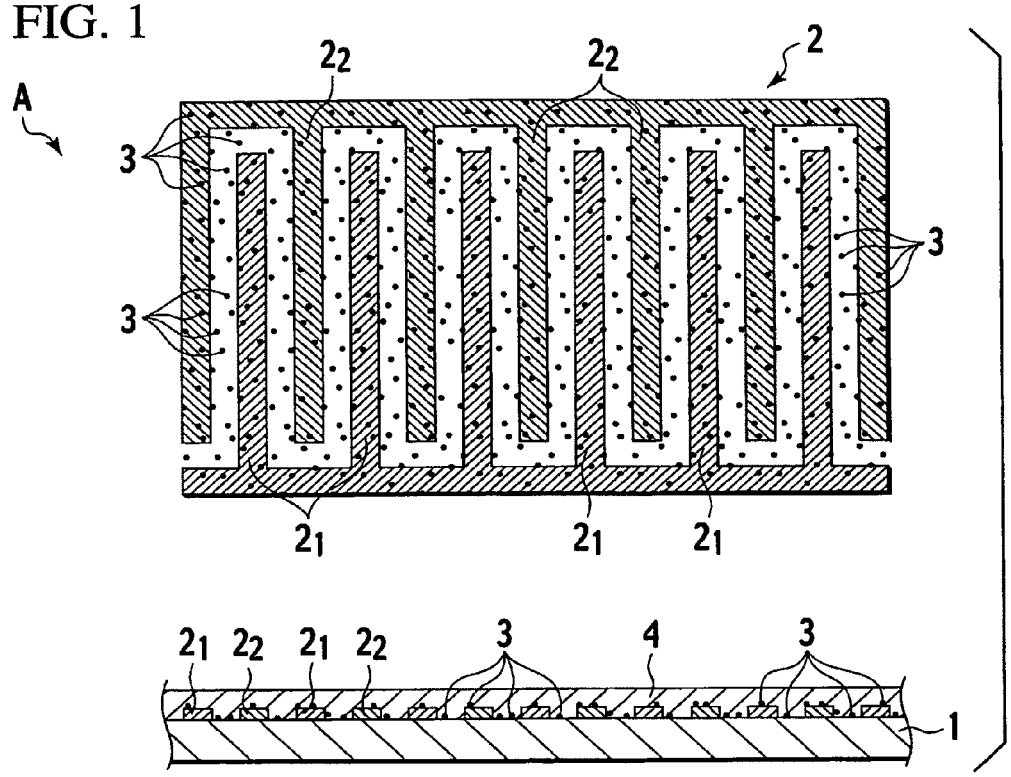
FIG. 1 is a schematic illustration showing a first element structure of the present invention.

In a proton acceptance type gas sensor of the present invention, protons are brought into contact with an organic compound containing an introduced heterocycle comprising a nitrogen atom, and the change in electrical resistivity, photoconductivity, or optical absorption band for the organic compound that accompanies proton addition is detected.

As follows is a description of the proton acceptance type gas sensor of the present invention, centered around a hydrogen gas sensor that uses a pyridine-modified pyrrolo-pyrrole pigment.

The inventors of the present invention have clarified the electronic structure (and in particular, the coloring within the solid state) of the known organic pigment pyrrolo-pyrrole (hereafter referred to as DPP), from the perspectives of molecular structure, crystalline structure, and intermolecular interaction, and have submitted many proposals based on applications of this structure. Moreover, the inventors also discovered that of the various DPPs, DPPs having a pyridine ring (preferably with the nitrogen atom at the para position) (hereafter referred to as pyridine-DPP or DPPP) react extremely sensitively with protons. In other words, a pyridine-DPP having a pyridine ring within the DPP skeleton exhibits an extremely high level of sensitivity to protons, and upon proton addition, undergoes large changes in electrical resistivity, photoconductivity, and optical absorption band at room temperature. The present invention has been completed on the basis of this finding, and is able to provide a highly reliable hydrogen gas sensor. As is disclosed in the reference {J. Mizuguchi, H. Takahashi and H. Yamakami: Crystal structure of 3,6-bis(4'-pyridyl)-pyrrolo[3,4-c]pyrrole-1,4-dione, Z. Krist. NCS 217, 519 to 520 (2002)}, pyridine-DPP can exist in two crystalline phases, but for the hydrogen gas sensor, the crystalline phase I (the crystalline phase in which the nitrogen atom of the pyridine ring does not form a NH—N hydrogen bond) is preferred.

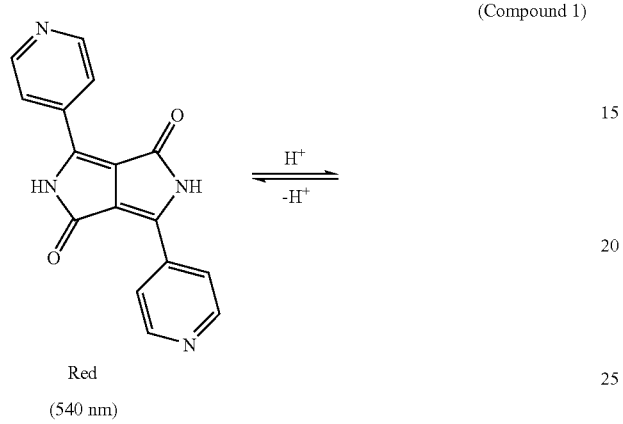

Pyridine-DPP is extremely stable relative to light and heat, but if a proton ($H^+$) appears, reacts immediately at room temperature, and the optical absorption band changes from 540 nm (red) to 580 nm (violet). Accompanying this change, the electrical resistivity falls by 3 to 5 orders of magnitude, and a large photoconductivity also emerges. Any of these phenomena can be used to provide a highly sensitive hydrogen gas sensor, that operates at room temperature.

The organic compound used in the present invention is preferably an organic pigment containing an introduced heterocycle comprising a nitrogen atom, and suitable examples include the aforementioned pyridine-DPP and derivatives thereof (compound 2), as well as pyridine-modified quinacridone and derivatives thereof (compound 3), indigo and derivatives thereof (compound 4), phthalocyanine and derivatives thereof (compound 5), anthraquinone and derivatives thereof (compound 6), indanthrone and derivatives thereof (compound 7), anthanthrone and derivatives thereof (compound 8), perylene and derivatives thereof (compound 9-1) and (compound 9-2), pyrazolone and derivatives thereof (compound 10), perinone and derivatives thereof (compound 11-1) and (compound 11-2), isoindolinone and derivatives thereof (compound 12), isoindoline and derivatives thereof (compound 13), dioxazine and derivatives thereof (compound 14), and other similar compounds.

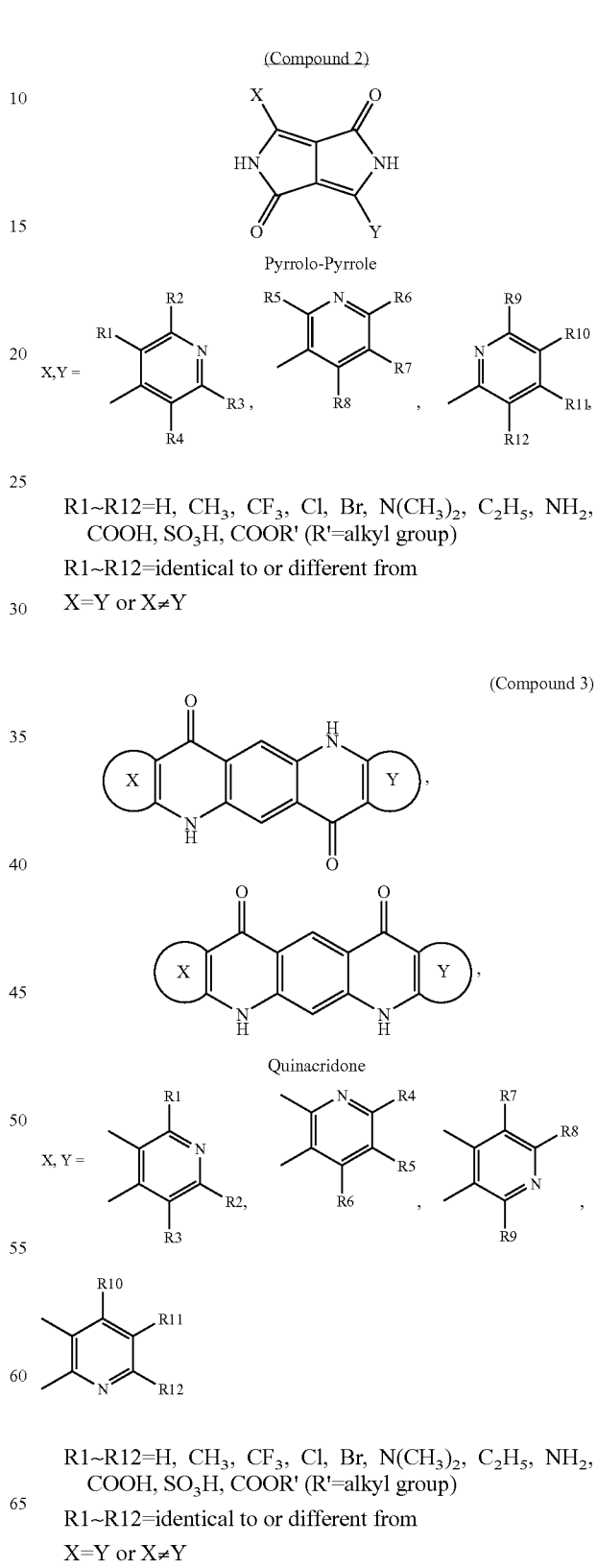

(Compound 4)

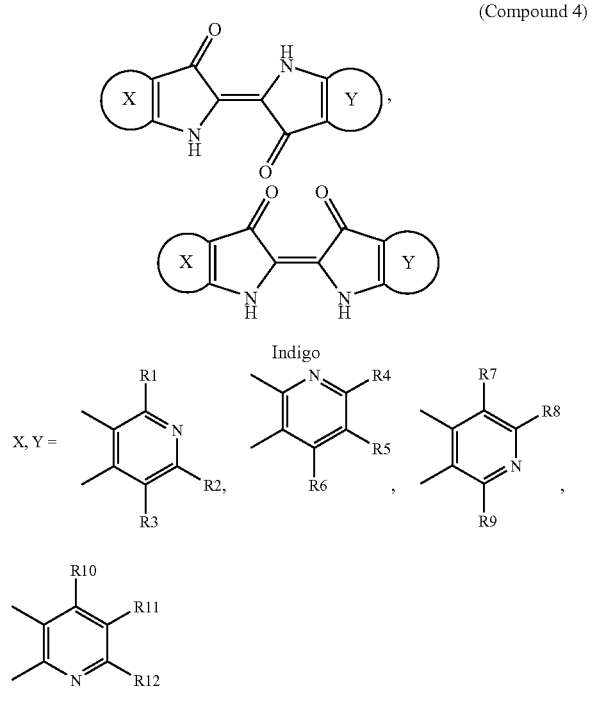

Indigo

R1~R12=H, CH₃, CF₃, Cl, Br, N(CH₃)₂, C₂H₅, NH₂, COOH, SO₃H, COOR' (R'=alkyl group)
R1~R12=identical to or different from
X=Y or X≠Y (Compound 5)

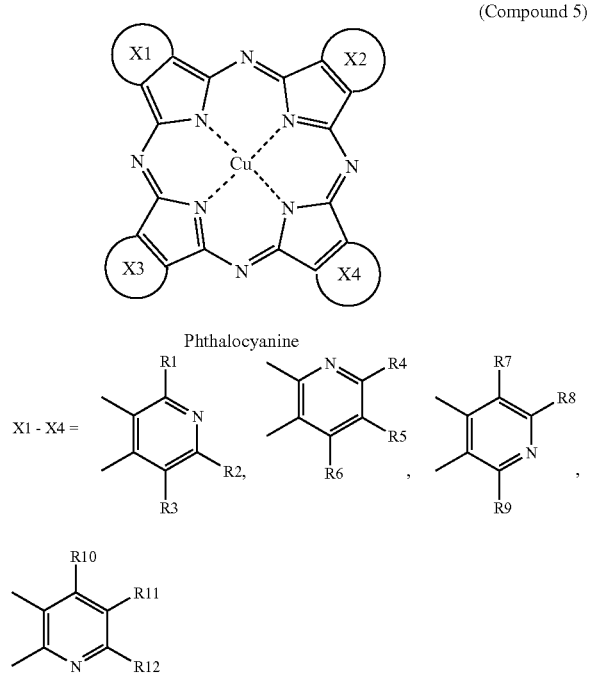

Phthalocyanine

R1~R12=H, CH₃, CF₃, Cl, Br, N(CH₃)₂, C₂H₅, NH₂, COOH, SO₃H, COOR' (R'=alkyl group)
R1~R12=identical to or different from
X1~X4=identical to or different from (Compound 6)

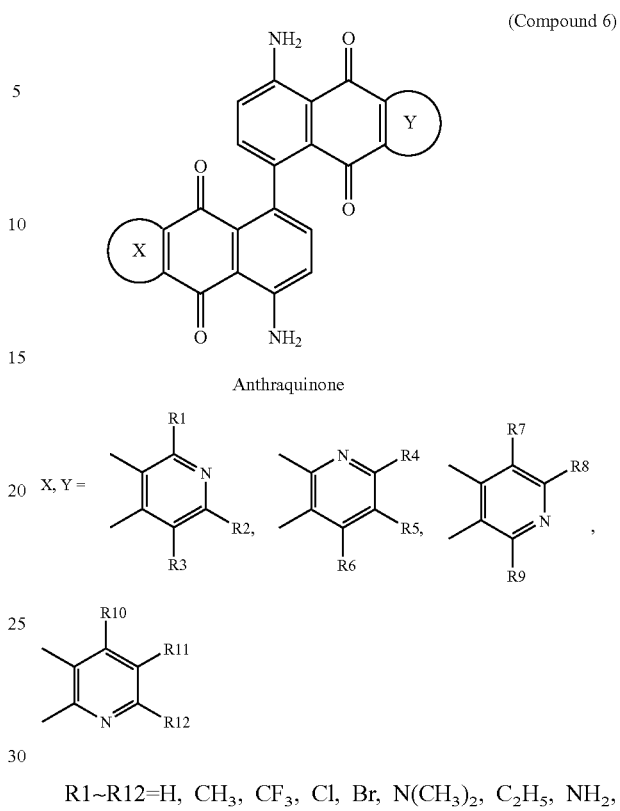

Anthraquinone

R1~R12=H, CH₃, CF₃, Cl, Br, N(CH₃)₂, C₂H₅, NH₂, COOH, SO₃H, COOR' (R'=alkyl group)
R1~R12=identical to or different from
X=Y or X≠Y (Compound 7)

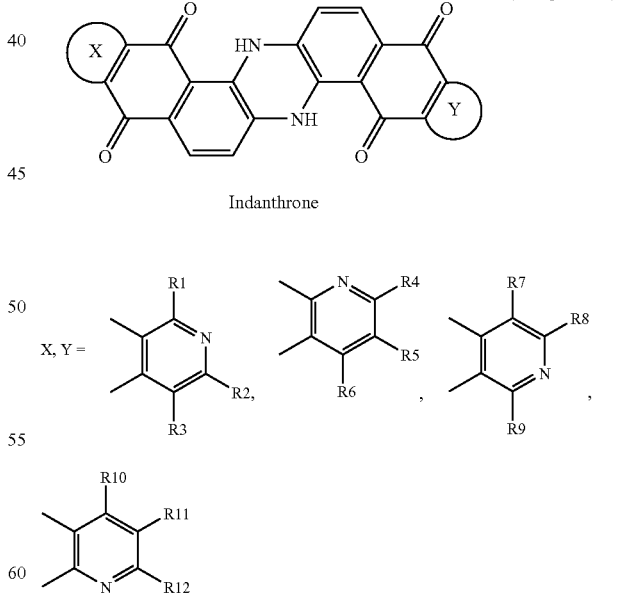

Indanthrone

R1~R12=H, CH₃, CF₃, Cl, Br, N(CH₃)₂, C₂H₅, NH₂, COOH, SO₃H, COOR' (R'=alkyl group)
R1~R12=identical to or different from
X=Y or X≠Y (Compound 8)

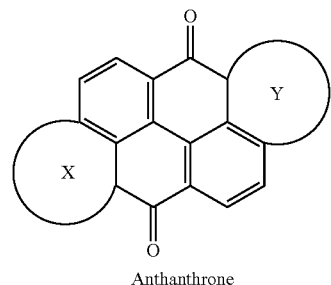

Anthanthrone

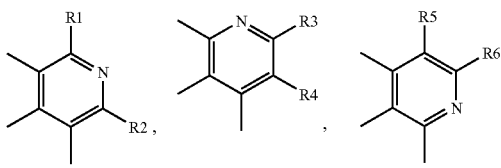

R1~R6=H, CH₃, CF₃, Cl, Br, N(CH₃)₂, C₂H₅, NH₂, COOH, SO₃H, COOR' (R'=alkyl group)
R1~R6=identical to or different from
X=Y or X≠Y (Compound 9-1)

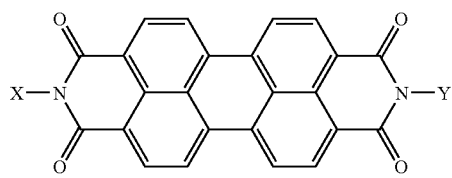

Perylene

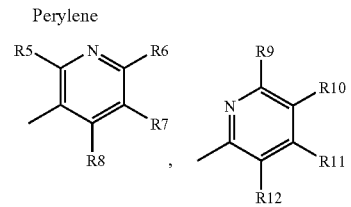

R1~R12=H, CH₃, CF₃, Cl, Br, N(CH₃)₂, C₂H₅, NH₂, COOH, SO₃H, COOR' (R'=alkyl group)
R1~R12=identical to or different from
X=Y or X≠Y (Compound 9-2)

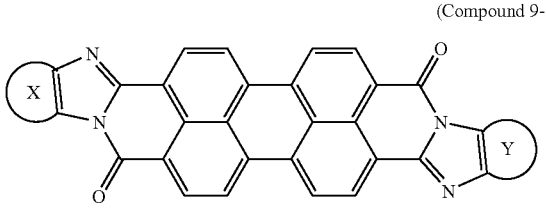

Perylene

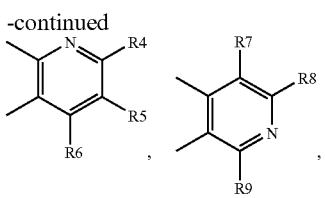

R1~R12=H, CH₃, CF₃, Cl, Br, N(CH₃)₂, C₂H₅, NH₂, COOH, SO₃H, COOR' (R'=alkyl group)
R1~R12=identical to or different from
X=Y or X≠Y (Compound 10)

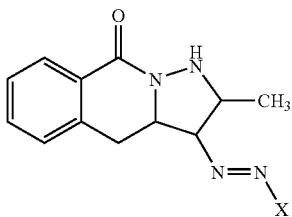

Pyrazolone $R1 \sim R12 = H, CH_3, CF_3, Cl, Br, N(CH_3)_2, C_2H_5, NH_2, COOH, SO_3H, COOR'$ (R'=alkyl group)
R1~R12=identical to or different from (Compound 11-1)

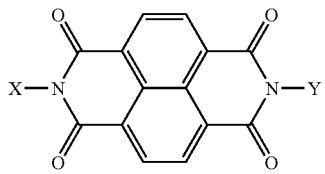

Perinone $R1 \sim R12 = H, CH_3, CF_3, Cl, Br, N(CH_3)_2, C_2H_5, NH_2, COOH, SO_3H, COOR'$ (R'=alkyl group)
R1~R12=identical to or different from
X=Y or X≠Y (Compound 11-2)

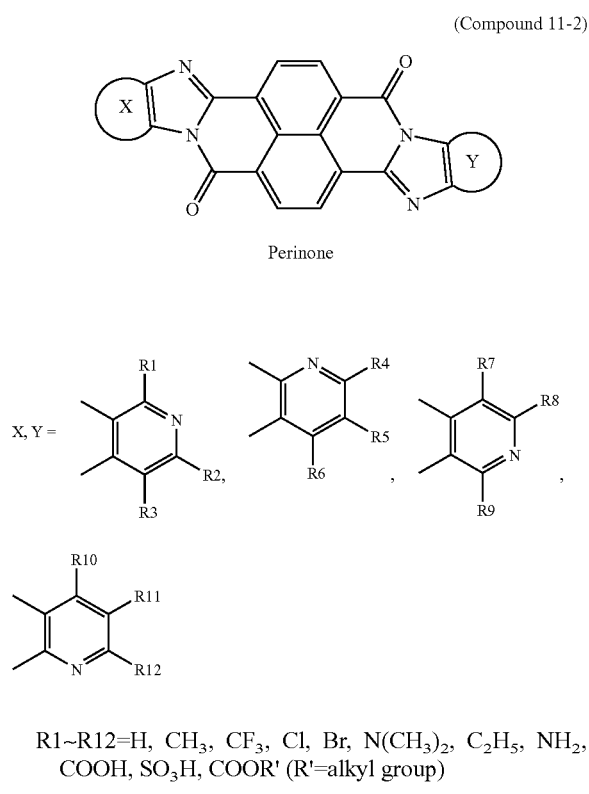

Perinone

R1~R12=H, CH$_3$, CF$_3$, Cl, Br, N(CH$_3$)$_2$, C$_2$H$_5$, NH$_2$, COOH, SO$_3$H, COOR' (R'=alkyl group)
R1~R12=identical to or different from
X=Y or X≠Y (Compound 12)

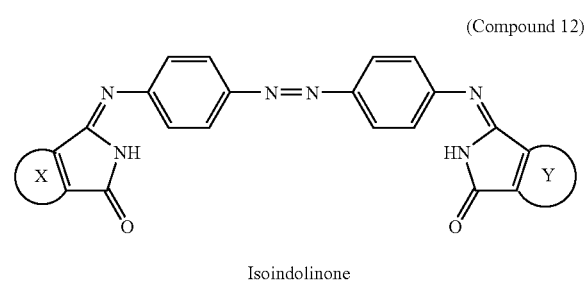

Isoindolinone

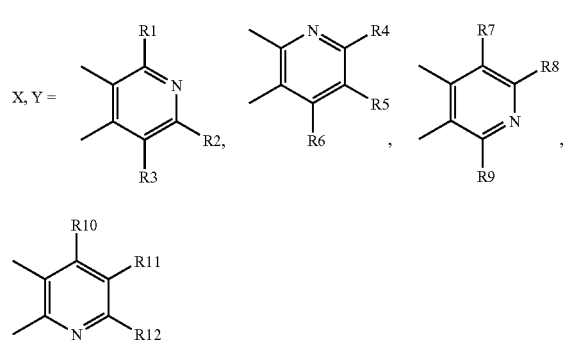

R1~R12=H, CH$_3$, CF$_3$, Cl, Br, N(CH$_3$)$_2$, C$_2$H$_5$, NH$_2$, COOH, SO$_3$H, COOR' (R'=alkyl group)
R1~R12=identical to or different from
X=Y or X≠Y (Compound 13)

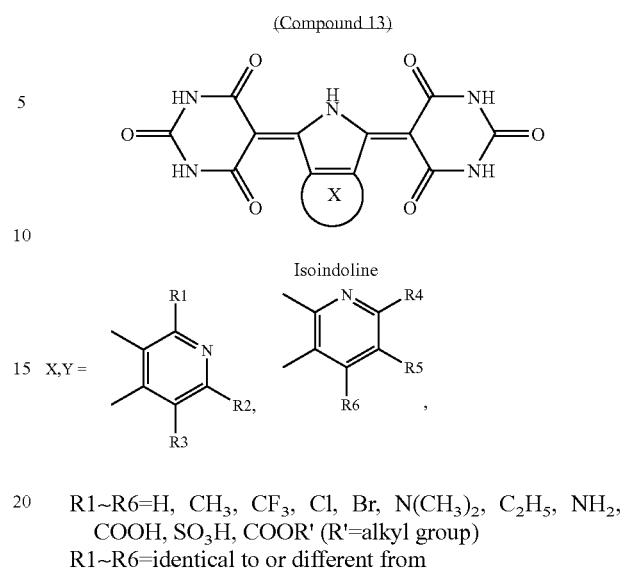

Isoindoline

R1~R6=H, CH$_3$, CF$_3$, Cl, Br, N(CH$_3$)$_2$, C$_2$H$_5$, NH$_2$, COOH, SO$_3$H, COOR' (R'=alkyl group)
R1~R6=identical to or different from (Compound 14)

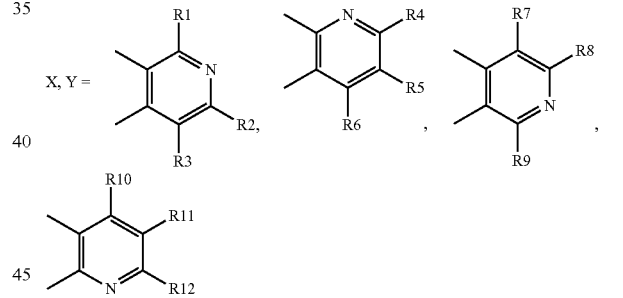

Dioxazine

R1~R12=H, CH$_3$, CF$_3$, Cl, Br, N(CH$_3$)$_2$, C$_2$H$_5$, NH$_2$, COOH, SO$_3$H, COOR' (R'=alkyl group)
R1~R12=identical to or different from
X=Y or X≠Y In addition, the organic compound selected in the present invention is not limited to the above compounds. The organic compound selected in the present invention is an organic compound that contains an introduced heterocycle comprising a nitrogen atom, and preferably a pyridine-based heterocycle. For example, organic compounds having the following types of nitrogen atom-containing six-membered rings (which are also referred to as pyridine-based heterocycles in the present invention) (compound 15), or organic compounds having a condensed ring structure comprising a nitrogen atom, such as cinnoline (compound 16), phthalazine (compound 17), or phenazine (compound 18) are also suitable.

Specific examples include compounds of the above (compound 2) through (compound 14), in which the pyridine ring has been substituted with any one of (compound 15) through (compound 18).

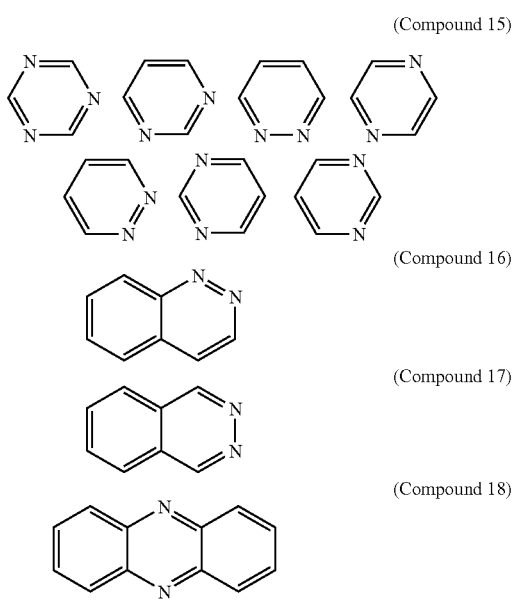

(Compound 15)

(Compound 16)

(Compound 17)

(Compound 18)

DPP having a pyridine ring can be synthesized, for example, in accordance with the method disclosed in Japanese Patent Publication (B2) No. Kokoku Hei 4-25273, from cyanopyridine and succinic acid. In addition, other organic compounds containing nitrogen atoms can be synthesized, for example, in accordance with the methods disclosed in W. Herbst and K. Hunger, Industrial Organic Pigments-Production, Properties, Applications-, VCH Weinheim, New York, Basel, Cambridge (1993).

The following description focuses on the example of pyridine-DPP, but the basic process of the present invention comprises the following two steps, wherein the first step is a step for dissociating and protonating the hydrogen gas (hydrogen molecules) ($H_2 \rightarrow H+H \rightarrow 2H^+ + 2e$), and the second step is a step for detecting the changes in physical properties that accompany the addition of the protons to the pyridine-DPP.

In the first step, the protonation of hydrogen gas can be problematic, but this problem can preferably be resolved by using a catalyst such as Pt, Pd, Ni, a two-component alloy thereof, or a three-component alloy thereof. In other words, on contact with these metals, the hydrogen molecules become unstable, and are protonated via atomic-state hydrogen (H). Specifically, the protonation of hydrogen gas can be accelerated by the sputtering of Pd or Pt.

The element structure in the second step is basically an element comprising at least one pair of electrodes, with pyridine-DPP disposed between the electrodes, and an aforementioned catalyst for protonating the hydrogen gas disposed in an islands-type arrangement. In this description, the term "islands-type arrangement" refers to a state in which a film produced by sputtering contains metal particles scattered in an islands-type pattern in insufficient quantity to generate electrical continuity.

Accordingly, in a hydrogen gas sensor of the present invention, the organic compound and the hydrogen gas protonation catalyst are preferably in contact.

The hydrogen gas sensor of the present invention is preferably a hydrogen gas sensor wherein at least one pair of electrodes is positioned in contact with the above film of the organic compound, and the change in electrical resistivity or photoconductivity is detected. Furthermore, the hydrogen gas sensor of the present invention is even more preferably a hydrogen gas sensor which is an element in which at least one pair of electrodes is positioned in an opposing arrangement on top of a substrate, the above film of the organic compound is disposed thereon, and either a protonation catalyst contacts one surface or both surfaces of the film of the organic compound, or a protonation catalyst is distributed through the organic compound layer, wherein the sensor is an electrical resistance-mode sensor that detects changes in the electrical resistivity between the electrodes. The film of the organic compound can be provided by a vacuum deposition method or a sputtering method, but is preferably provided using a vacuum deposition method. Furthermore, the protonation catalyst can be provided in an islands-type arrangement, either on top of the substrate and the electrodes, or on top of the film of the organic compound, or within the film of the organic compound, either using a vacuum deposition method or a sputtering method, and preferably using a sputtering method.

One specific example is shown in FIG. 1, which shows an element structure (A) wherein interdigital electrodes (2, $2_1$, $2_2$) are positioned in an alternating arrangement on top of a substrate (1) of glass or the like, a catalyst such as Pd (3) or the like is deposited by sputtering (approximately several Å) in an islands-type arrangement (using an E-1030 ion sputtering apparatus, manufactured by Hitachi, Ltd.), and a film of pyridine-DPP (4) is then provided on top by vacuum deposition (within a range from approximately several Å to several hundred Å) (using an EG240 apparatus, manufactured by Tokyo Vacuum Co., Ltd.). The pyridine-DPP is the aforementioned compound 2 wherein X=Y, and X is a pyridine ring with the nitrogen atom in the para position. Moreover, $R_1=R_2=R_3=R_4=H$. In this example, satisfactory sensitivity was obtained at room temperature in a 1% hydrogen gas atmosphere.

The surface area (of the electrode portion) of the element showed in FIG. 1 is 5 mm×10 mm, and the width of the electrodes and the spacing between electrodes is 100 μm.

Figure 2:
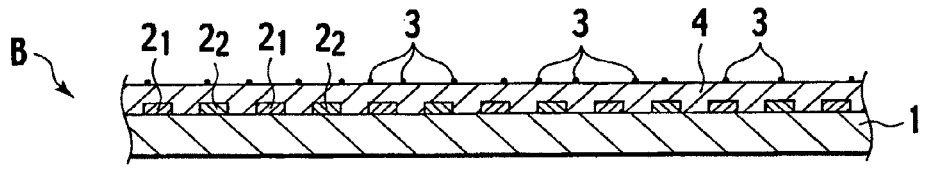
FIG. 2 is a schematic illustration showing a second element structure of the present invention.

Furthermore, a second example is shown in FIG. 2, which shows an element structure (B) in which a film of pyridine-DPP (4) is deposited on top of the electrodes (2, $2_1$, $2_2$), and Pd (3) is then sputtered thereon in an islands-type arrangement.

Figure 3:
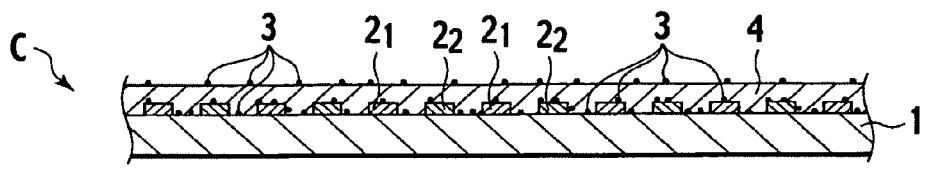
FIG. 3 is a schematic illustration showing a third element structure of the present invention.

In addition, a third example is shown in FIG. 3, which shows an element structure (C) in which the protonation catalyst is distributed within the film of the organic compound. There are no particular restrictions on the electrodes, and suitable materials include Al, ITO (Indium-Tin-Oxide: a transparent electrode), Au, Ag, Pd, Pt, and Pd—Pt alloy. An electrical resistance-mode hydrogen gas sensor is completed by detecting the change in electrical resistivity between the electrodes. A hydrogen gas sensor of this structure can, of course, also detect the vapor-state proton gas seen with acids, meaning the same element structure also functions as an acid sensor.

Needless to say, a photoconduction-mode hydrogen gas sensor that includes an excitation light source, and an optical absorption band-mode hydrogen gas sensor that includes a photodiode or a photomultiplier or the like can also be provided. In a similar manner to the sensor described above, these elements can, of course, also function as acid sensors.

Figure 9:
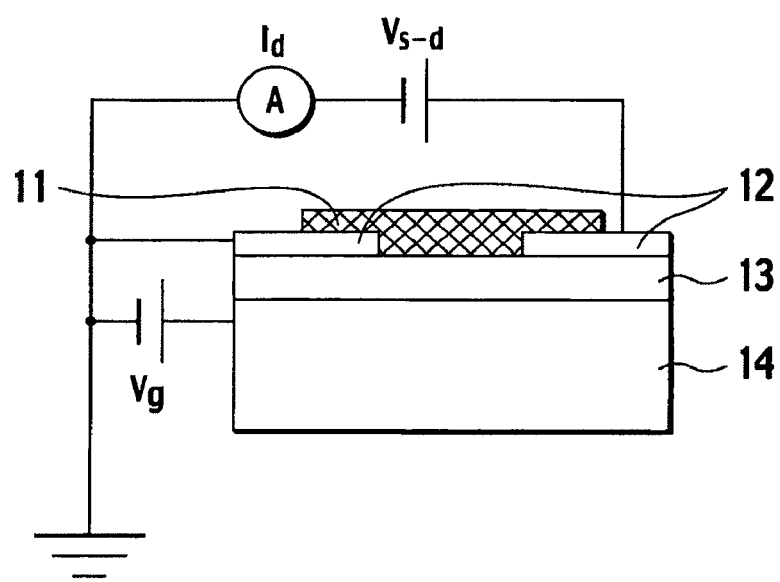
FIG. 9 is a schematic illustration showing a fourth element structure of the present invention.

In addition, a fourth example is shown in FIG. 9. The hydrogen gas sensor shown in FIG. 9 is a sensor with a so-called organic FET (field-effect transistor) structure. Hydrogen gas sensors in which a protonation catalyst is sputtered onto an element having the electrodes positioned in an FET structure, and an organic compound layer is then formed thereon have been shown to offer further improvements in sensitivity. In the hydrogen gas sensor shown in FIG. 9, a n⁺—Si substrate (14) functions as the gate, the source and drain electrodes (12) are formed on top of the substrate with a silicon oxide insulating film (13) disposed therebetween, and the above two-layer film (the protonation catalyst layer formed in an islands-type pattern and the organic compound layer) (11) is formed between the source and the drain. In the figure, Vg, Id, and Vs-d refer to the gate voltage, the drain current, and the source-drain voltage respectively. By controlling the gate voltage, this type of sensor with an FET structure is capable of a several-fold improvement in the level of sensitivity compared with that offered by the interdigital electrode-only sensor described above.

In a more detailed description of the principles of the present invention using the example of FIG. 1, the hydrogen gas first adsorbs to the surface of the pyridine-DPP (4), and then diffuses into the interior of the pyridine-DPP (4). Subsequently, the hydrogen gas encounters the Pd (3), where it dissociates and is converted to protons ($H_2 \rightarrow H+H$ (dissociation)$\rightarrow 2H^+ + 2e$ (protonation)). These protons undergo proton addition to the nitrogen atom of the pyridine ring of the pyridine-DPP (4). The electrons released at this point cause the electrical resistivity of the pyridine-DPP (4) to decrease by 2 to 4 orders of magnitude at room temperature. This decrease in the resistivity is then detected electrically, enabling a hydrogen gas sensor to be formed.

Figure 4:
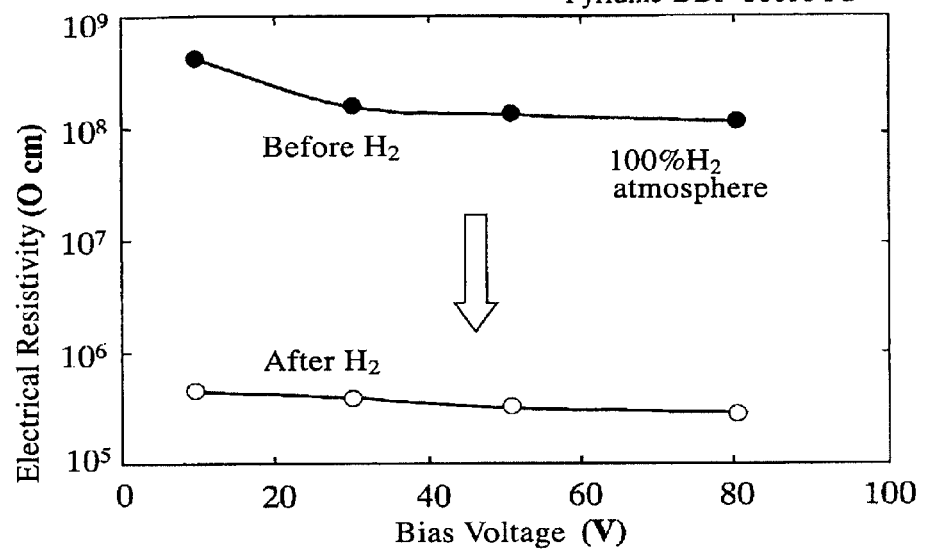
FIG. 4 is a diagram showing change in electrical resistivity within a pyridine-DPP element (catalyst: Pd) of FIG. 1.
Figure 5:
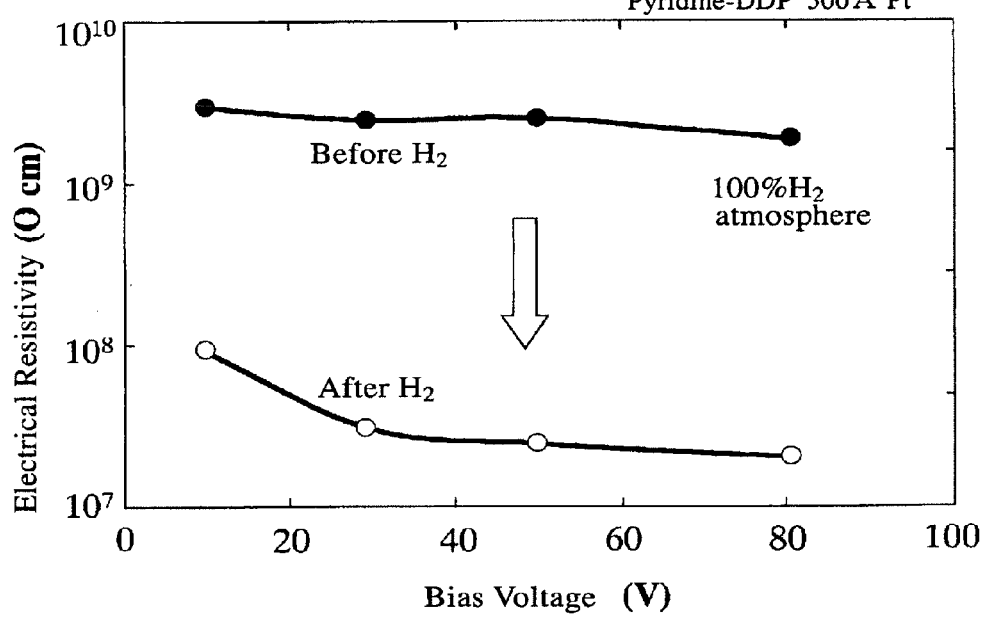
FIG. 5 is a diagram showing change in electrical resistivity within a pyridine-DPP element (catalyst: Pt) of FIG. 1.

FIG. 4 is a graph showing the change in resistivity for one example of the element shown in FIG. 1 under a 100% $H_2$ atmosphere, wherein the electrodes were ITO, the thickness of the pyridine-DPP was 500 Å, and Pd was used as the catalyst. Furthermore, FIG. 5 shows the results of a similar experiment in which Pt was used as the catalyst. In the figures, a (the black circles) shows the results before proton addition, and b (the white circles) shows the results after proton addition.

When the nitrogen atom of the pyridine ring of the pyridine-DPP undergoes proton addition, not only does the electrical resistivity value fall in the manner described above, but photoconductivity also emerges. Furthermore, the visible optical absorption band of the pyridine-DPP that occurs in the vicinity of 540 nm shifts to 580 nm, and the coloring of the band changes from red to violet. Accordingly, the detection method for the hydrogen gas sensor can employ any one of the change in electrical resistivity (electrical resistance mode), the emergence of photoconductivity (photoconduction mode), or the wavelength lengthening of the optical absorption band (540 nm→580 nm) (color change mode) as the detection function.

Figure 6:
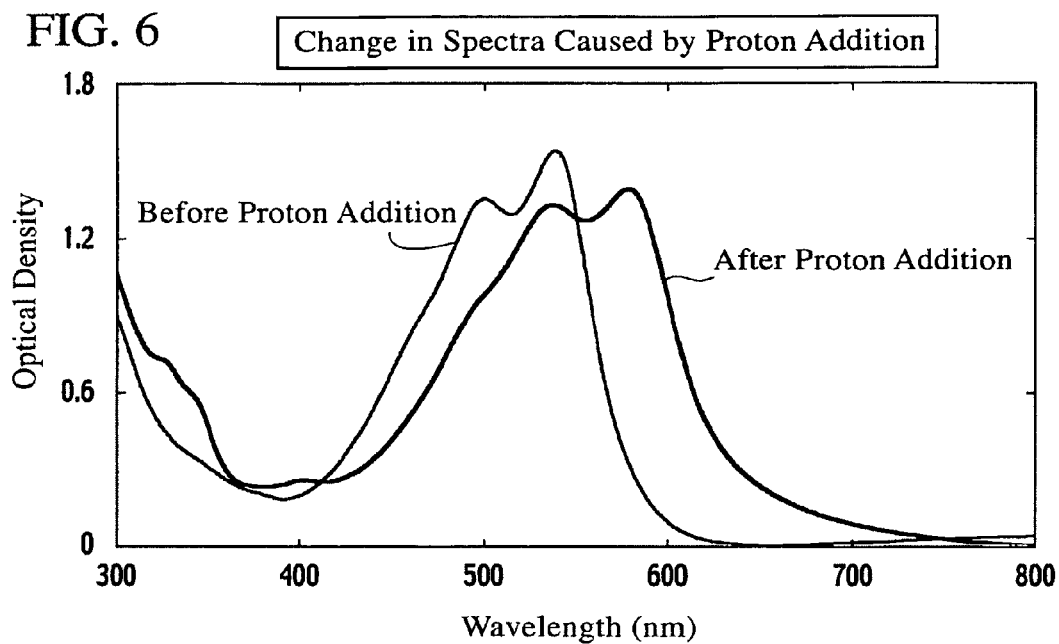
FIG. 6 shows absorption spectra before and after proton addition to pyridine-DPP.
Figure 7:
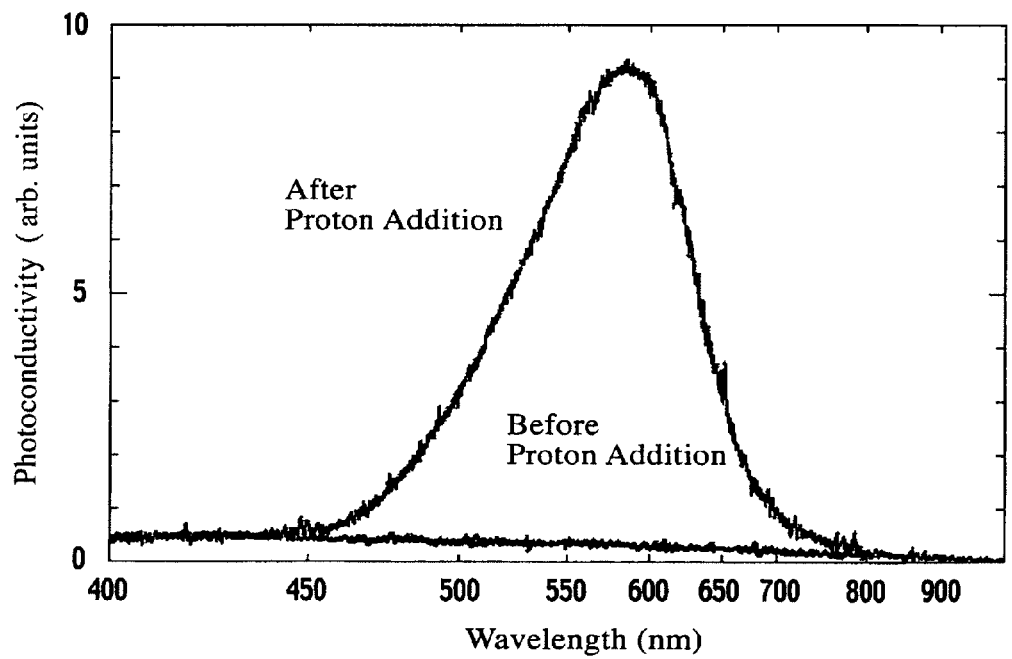
FIG. 7 shows photoconduction spectra before and after proton addition to pyridine-DPP.

FIG. 6 shows absorption spectra before and after proton addition to a pyridine-DPP deposition film (thickness: 1,200 Å) using $HNO_3$ vapor, and FIG. 7 shows photoconduction spectra.

Figure 10:
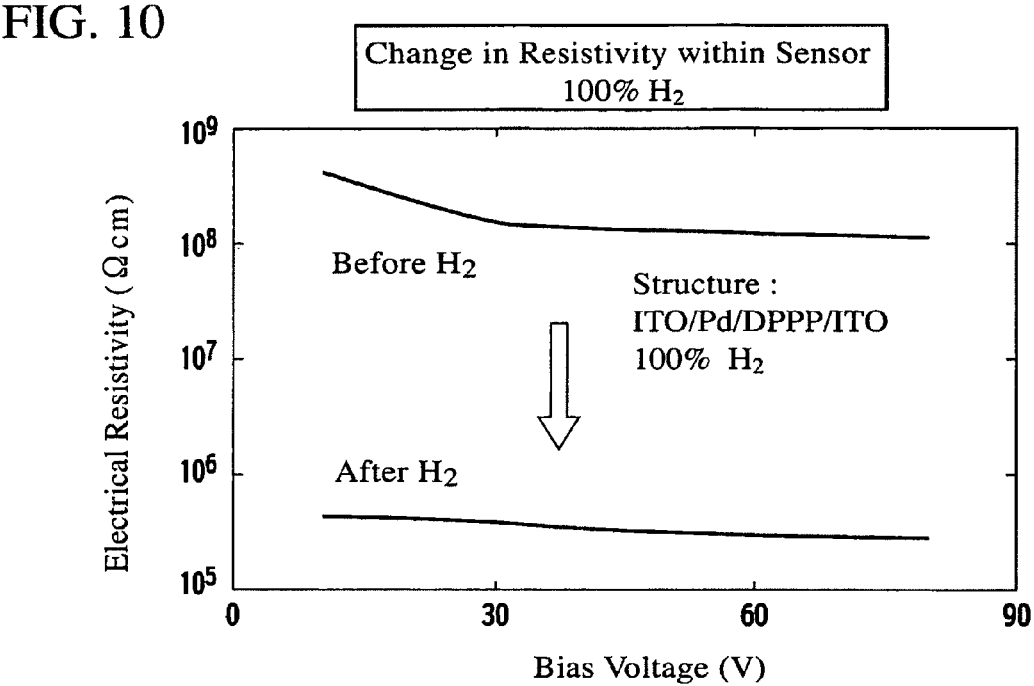
FIG. 10 is a diagram showing change in electrical resistivity within a pyridine-DPP element (catalyst: Pd) of FIG. 1.

FIG. 10 is a graph showing the change in electrical resistivity for another example of the element shown in FIG. 1 under a 100% $H_2$ atmosphere, wherein the electrodes were ITO, the thickness of the pyridine-DPP was 500 Å, and Pd was used as the catalyst. The pyridine-DPP is the aforementioned compound 2 wherein X=Y, and X is a pyridine ring with the nitrogen atom in the para position. Moreover, $R_1=R_2=R_3=R_4=H$. In this example, the pyridine-DPP used had been purified by sublimation.

Figure 11:
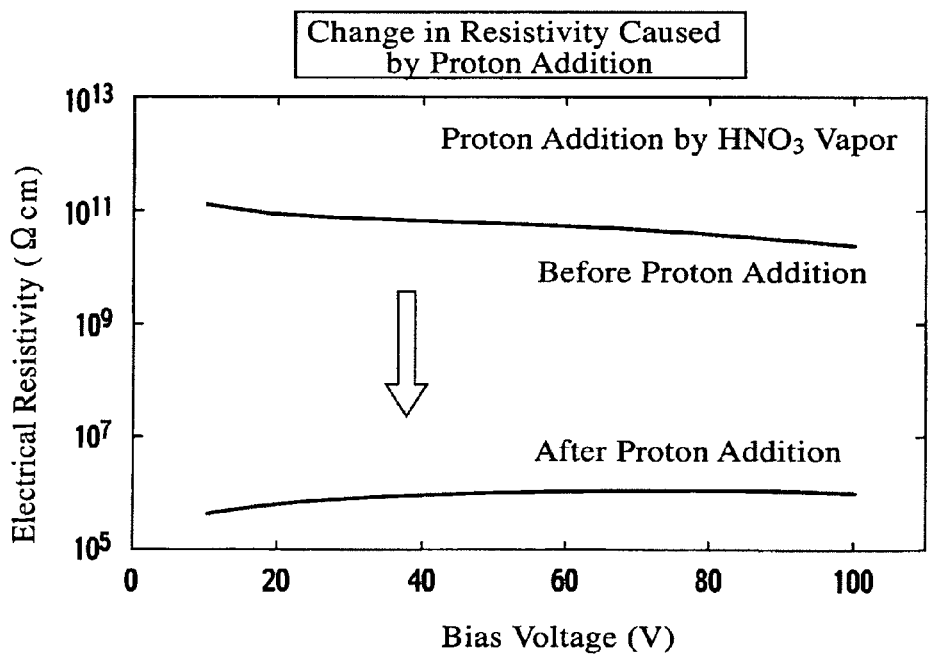
FIG. 11 shows electrical resistivity before and after proton addition to pyridine-DPP.

FIG. 11 is a graph showing the change in electrical resistivity accompanying proton addition to a pyridine-DPP deposition film (thickness: 1,200 Å) using $HNO_3$ vapor.

Figure 12:
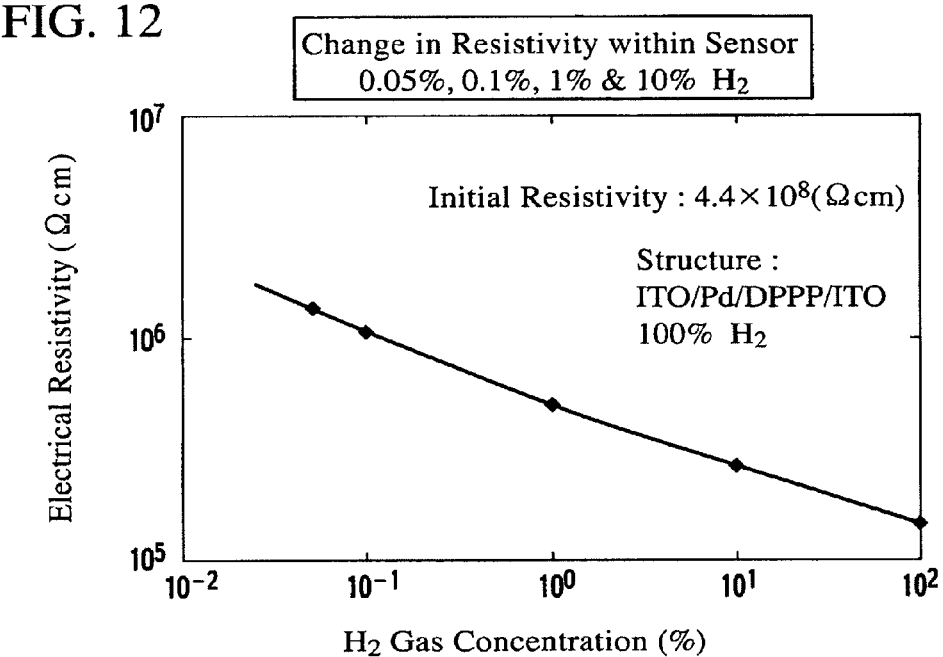
FIG. 12 is a diagram showing the hydrogen gas concentration dependency of the change in electrical resistivity within a pyridine-DPP element (catalyst: Pd) of FIG. 1.

FIG. 12 is a graph showing the hydrogen gas concentration dependency of the change in electrical resistivity for another example of the element shown in FIG. 1, wherein the electrodes were ITO, the thickness of the pyridine-DPP was 500 Å, and Pd was used as the catalyst.

Figure 13:
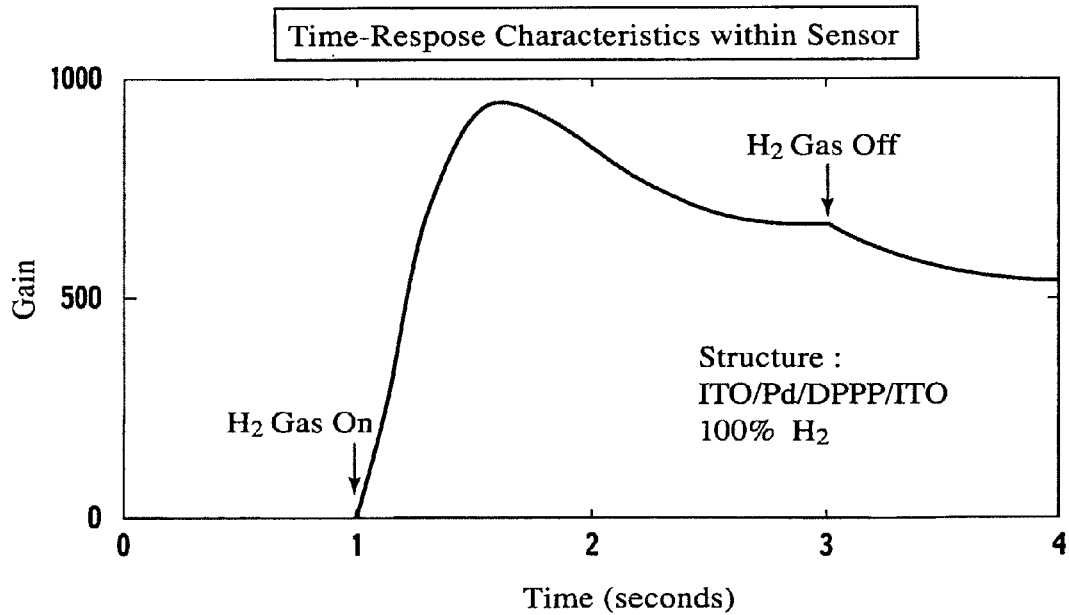
FIG. 13 is a diagram showing the time-response characteristics of the electrical resistivity within a pyridine-DPP element (catalyst: Pd) of FIG. 1.

FIG. 13 is a graph showing the time-response characteristics for another example of the element shown in FIG. 1, wherein the electrodes were ITO, the thickness of the pyridine-DPP was 500 Å, and Pd was used as the catalyst.

Figure 14:
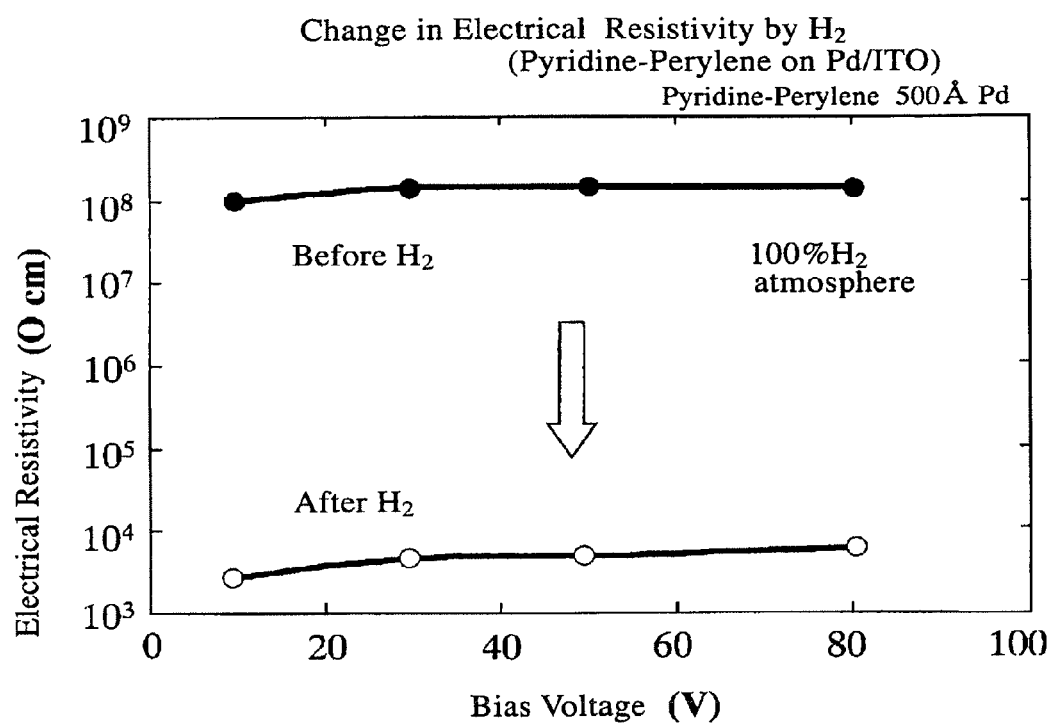
FIG. 14 is a diagram showing change in electrical resistivity within a pyridine-perylene element (catalyst: Pd) of FIG. 1.

FIG. 14 is another example with the element structure shown in FIG. 1, and shows the change in electrical resistivity for an element that uses pyridine-perylene instead of pyridine-DPP as the organic compound. Pyridine-perylene is the aforementioned compound 9-1 wherein X=Y, and X is a pyridine ring with the nitrogen atom in the para position. Moreover, $R_1=R_2=R_3=R_4=H$. The electrodes were ITO, the thickness of the pyridine-perylene was 500 Å, and Pd was used as the catalyst. In the figure, a (the black circles) shows the results before proton addition, and b (the white circles) shows the results after proton addition. The electrical resistivity of the pyridine-perylene changes by a factor of approximately 20.000-fold or greater depending on the presence or absence of hydrogen gas. In a similar manner to the case of pyridine-DPP, an element that uses pyridine-perylene also exhibits the same reaction when Pt is used as the catalyst.

Furthermore, when any of the other various organic compounds described above are used, then in a similar manner to that observed for pyridine-DPP and pyridine-perylene, a dramatic change in the electrical resistivity can be noted depending on the presence or absence of hydrogen gas.

In order to raise the sensitivity of the sensor, a thin film of an organic pigment such as a phthalocyanine can be provided as a sensitivity promoter, either on the upper surface or lower surface of the pyridine-DPP, or on both surfaces of the pyridine-DPP. Furthermore, co-deposition of the pyridine-DPP and a phthalocyanine is also possible. The ratio between the pyridine-DPP and the phthalocyanine is typically equivalent to a film thickness ratio of approximately 10:1, and in the case of co-deposition, the weight ratio is approximately 10:1.

The above description of the present invention focused on a sensor for detecting hydrogen gas that uses pyridine-DPP as an organic compound containing an introduced heterocycle comprising a nitrogen atom, but as mentioned above, the heterocycle comprising a nitrogen atom is not limited to pyridine, and other compounds such as the aforementioned triazine, pyrazine, pyrimidine, and pyridazine can also be used. Furthermore, the gas that is detected is not limited to hydrogen gas, and any gas that dissociates and generates protons, including nitric acid gas, hydrogen chloride gas, and hydrogen fluoride gas can also be detected using a sensor of the present invention.

The present invention can provide a low-cost hydrogen sensor that exhibits favorable sensory selectivity for protons, and can also provide a sensor capable of fulfilling the important functions of detecting hydrogen gas and preventing leakage accidents in modern production plants that use hydrogen gas as a carrier, in hydrogen gas storage facilities, and in so-called fuel cells that use hydrogen gas as an energy source. Furthermore, the present invention is not limited to hydrogen sensors, and can provide high-sensitivity proton acceptance type gas sensors at low cost for a wide variety of applications, including acid sensors, meaning the invention can also provide sensors capable of fulfilling the important functions of detecting a variety of proton-donating gases and preventing leakage accidents in production plants in which there is a possibility of the generation of toxic gases such as nitric acid gas, hydrogen fluoride gas, or hydrogen chloride gas.

EXAMPLES

Example 1

1. Electrical Resistance Mode

When an element with the structure shown in FIG. 1 is placed in an atmosphere containing hydrogen gas, nitric acid gas, hydrogen chloride gas, hydrogen fluoride gas, or ammonia gas or the like, the electrical resistivity falls rapidly. Because the electrical resistivity of pyridine-DPP is normally extremely high, and close to that of an insulator, a voltage is applied across the electrodes, and the minute current that flows is detected. In other words, by detecting and amplifying any changes in this minute current, the element can be used as a sensor. In an element of the present invention, the change in electrical resistivity is within a range from 1 to 4 or more orders of magnitude, and is consequently extremely easy to detect. The detection system, namely the input system, is of high impedance, and the circuit design preferably takes this factor into account. For example, an arrangement in which a buffer that uses a high input impedance OP amplifier is placed in a stage prior to the detection signal amplification circuit, enabling impedance conversion to be conducted, is effective.

Figure 8:
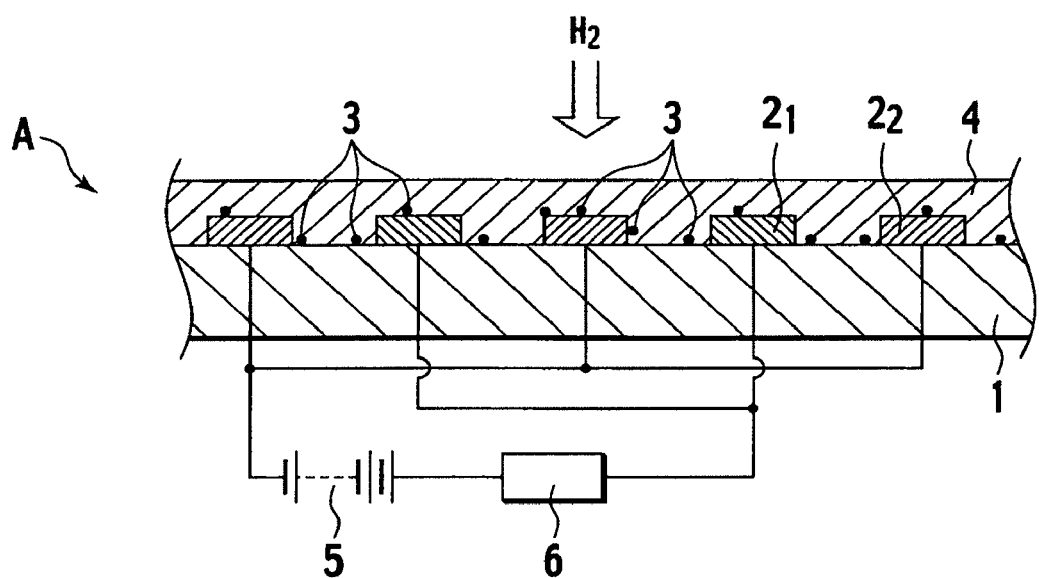
FIG. 8 is a schematic illustration of a circuit for detecting changes in electrical resistance.

A specific circuit is the circuit shown in FIG. 8, which uses the element shown in FIG. 1, and in this circuit, the opposing electrodes ($2_1$, $2_2$) are connected in an alternating arrangement, one of these electrodes is connected to the negative electrode of a power source (5), and the other electrode is connected to the positive electrode. A detection circuit (6) that detects the current is included within the closed circuit comprising these electrodes and the power source, enabling the detection of variations in the current caused by changes in the electrical resistivity of the pyridine-DPP/Pd.

Example 2

2. Photoconduction Mode

The structure of the element is the same as that for the electrical resistance mode, with the exceptions that the substrate was a glass plate, and ITO was used as the electrodes. When this element is irradiated with visible light, the electrical resistance decreases dramatically (a photoconduction phenomenon), enabling hydrogen gas to be detected.

Example 3

3. Absorption Band Mode

In this optical absorption band mode, electrodes are unnecessary, and the remaining structures are the same as those for the electrical resistance mode and photoconduction mode. When proton addition occurs within the pyridine-DPP film, the 540 nm absorption band shifts to 580 nm, and this mode detects this change in the optical absorption band using a semiconductor detector or a photomultiplier, enabling use as a hydrogen gas sensor.

Both the electrical resistance mode and the photoconduction mode basically use a change in the electrical resistance as the sensor. The mode of operation can use a detection method that uses either a direct current or an alternating current.

INDUSTRIAL APPLICABILITY

The present invention provides a low-cost proton acceptance type gas sensor, and in particular a hydrogen gas sensor, which exhibits favorable sensory selectivity for protons, can use a variety of different detection devices, detects changes using an electrical resistance mode, a photoconduction mode, or an optical absorption band mode, and contributes significantly to the detection of hydrogen gas and the prevention of leakage accidents, and as such, can be used across an extremely broad range of applications. Furthermore, the sensor is also effective as an acid sensor for hydrogen fluoride gas and the like.

What is claimed is:

1. A proton acceptance type gas sensor, comprising an organic compound containing an introduced heterocycle comprising a nitrogen atom, and a protonation catalyst in an islands-type arrangement, wherein the organic compound and the protonation catalyst contact each other, and a change in electrical resistivity, photoconductivity, or optical absorption band for the organic compound accompanies proton addition to the organic compound.

2. The proton acceptance type gas sensor according to claim 1, wherein at least one pair of electrodes is positioned in contact with a film of the organic compound, and a change in electrical resistivity or photoconductivity is detected.

3. The proton acceptance type gas sensor according to claim 1, which is an element in which at least one pair of comb-shaped electrodes is positioned in an opposing arrangement on top of a substrate, a film of the organic compound is disposed thereon, and either a protonation catalyst contacts one surface or both surfaces of the film of the organic compound, or a protonation catalyst is distributed through the film of the organic compound, wherein the sensor is an electrical resistance-mode sensor that detects changes in electrical resistivity between the electrodes.

4. The proton acceptance type gas sensor according to claim 1, having a field-effect transistor structure in which a $n^+$-Si substrate functions as a gate, source and drain electrodes are formed on top of the substrate with a silicon oxide insulating film disposed therebetween, and a film of the organic compound is formed on top of the silicon oxide and the electrodes.

5. The proton acceptance type gas sensor according to claim 1, wherein a film of an organic pigment that acts as a sensitivity promoter is layered to either one surface or both surfaces of a film of the organic compound.

6. The proton acceptance type gas sensor according to claim 1, wherein the heterocycle comprising a nitrogen atom is a pyridine-based heterocycle.

7. The proton acceptance type gas sensor according to claim 1, wherein the organic compound is an organic pigment containing an introduced heterocycle comprising a nitrogen atom.

8. The proton acceptance type gas sensor according to claim 7, wherein the organic pigment is a pyrrolo-pyrrole, quinacridone, indigo, phthalocyanine, anthraquinone, indanthrone, anthanthrone, perylene, pyrazolone, perinone, isoindolinone, isoindoline, dioxazine, or a derivative thereof.

9. A proton acceptance type gas sensor, in which protons are brought into contact with an organic compound containing an introduced heterocycle comprising a nitrogen atom, and a change in electrical resistivity, photoconductivity, or optical absorption band for the organic compound that accompanies proton addition is detected, wherein the organic compound is an organic pigment containing an introduced heterocycle comprising a nitrogen atom, and the organic pigment is a quinacridone, indigo, phthalocyanine, anthraquinone, indanthrone, anthanthrone, perylene, pyrazolone, perinone, isoindolinone, isoindoline, dioxazine, or a derivative thereof, and wherein the proton acceptance type gas sensor further comprises a protonation catalyst in an islands-type arrangement, wherein the organic compound and the protonation catalyst contact each other.

10. The proton acceptance type gas sensor according to claim 9, wherein the heterocycle comprising a nitrogen atom is a pyridine-based heterocycle.

11. The proton acceptance type gas sensor according to claim 8, wherein the organic pigment is a quinacridone or a derivative thereof.

12. The proton acceptance type gas sensor according to claim 8, wherein the organic pigment is an indigo or a derivative thereof.

13. The proton acceptance type gas sensor according to claim 8, wherein the organic pigment is an anthraquinone or a derivative thereof.

14. The proton acceptance type gas sensor according to claim 8, wherein the organic pigment is an indanthrone or a derivative thereof.

15. The proton acceptance type gas sensor according to claim 8, wherein the organic pigment is an anthanthrone or a derivative thereof.

16. The proton acceptance type gas sensor according to claim 8, wherein the organic pigment is a perylene or a derivative thereof.

17. The proton acceptance type gas sensor according to claim 8, wherein the organic pigment is a pyrazolone or a derivative thereof.

18. The proton acceptance type gas sensor according to claim 8, wherein the organic pigment is a perinone or a derivative thereof.

19. The proton acceptance type gas sensor according to claim 8, wherein the organic pigment is an isoindolinone or a derivative thereof.

20. The proton acceptance type gas sensor according to claim 8, wherein the organic pigment is an isoindoline or a derivative thereof.

21. The proton acceptance type gas sensor according to claim 8, wherein the organic pigment is a dioxazine or a derivative thereof.

* * * * *